United States Patent [19]
Duranleau et al.

[11] 3,979,455
[45] Sept. 7, 1976

[54] PREPARATION OF DIOXYIMINO-CYCLOALKANONES AND RELATED INTERMEDIATES

[75] Inventors: Roger G. Duranleau, Ardonia, N.Y.; Dennis R. Taylor, Temple City, Calif.

[73] Assignee: Texaco Inc., New York, N.Y.

[22] Filed: Dec. 13, 1974

[21] Appl. No.: 532,358

[52] U.S. Cl. .................. 260/566 A; 260/247.5 R; 260/268 R; 260/293.79; 260/310 D; 260/326.85
[51] Int. Cl.² ...................................... C07C 131/02
[58] Field of Search ............... 260/566 A, 247.5 R, 260/268 R, 293.79, 310 D, 326.85

[56] References Cited
UNITED STATES PATENTS
2,999,875  9/1961  Ferris et al. .................... 260/560 A OTHER PUBLICATIONS
*Tetrahedron Letters,* No. 4, pp. 203–206 (1964).

*Primary Examiner*—Gerald A. Schwartz
*Attorney, Agent, or Firm*—T. H. Whaley; C. G. Ries; Bernard Marlowe

[57] ABSTRACT

Dioximinocycloalkanones are prepared by reacting nitrosyl chloride with an enamine with sequential hydrolysis of the reaction product.

9 Claims, No Drawings

PREPARATION OF DIOXYIMINO-CYCLOALKANONES AND RELATED INTERMEDIATES

BACKGROUND OF THE INVENTION

This invention relates to processes for preparing dioximinocycloalkanones (i.e. bis [hydroximino]cycloalkanones). The production of these oximino or isonitroso cycloalkanones has been proposed heretofore by reaction of a cycloalkanone, such as cyclohexanone, with nitrosyl chloride, alkyl nitrites, nitric oxide and hydrochloric acid or similar nitrosating agents. A discussion of this technique appears, for example, in U.S. Pat. No. 2,999,875 and U.S. Pat. No. 3,112,345.

Additionally, the preparation of the monooximo substituted ketone, 1-morpholinocyclohexen-(1)-on-(6)-oxime, by reaction of 1-morpholinocyclohexene and nitrosyl chloride in the presence of triethylamine and an inert solvent has been disclosed heretofore by Metzger, *Tetrahedron Letters* No. 4, pages 203–206 (1964).

The foregoing U.S. Pat. No. 3,112,345, discloses conversion of the dioximinocycloalkanones to the corresponding diamino alcohols by catalytic reduction. These latter compounds are disclosed as having value for use in forming soaps when combined with fatty acids and as absorbents for carbon dioxide from flue gas in the manufacture of dry ice. The former patent, U.S. Pat. No. 2,999,875, discloses the cleavage of the dioximinocycloalkanones to form compounds that are readily converted by reduction to alpha, omega-diamino acids, for example, the alpha, omega-diamino acid, lysine, when the starting material is cyclohexanone, or ornithine if the starting material is cyclopentanone. Ornithine may, in turn, be converted to arginine, by known methods, to produce lysine. Arginine and lysine are important nutritional supplements. Other reaction sequences for converting the foregoing and other dioximinocycloalkanones to useful products are also disclosed in U.S. Pat. No. 2,999,875.

The alkyl nitrites suggested heretofore for nitrosation of cycloalkanones are, it is noted, expensive and productive of reduced yields of the desired dioximino products with significant loss of nitrogen oxide. In addition, the alkyl nitrites are dangerous to handle in that they tend to cause a marked fall in blood pressure; and in larger concentrations tend to produce methemoglobinemia resulting in cyanosis and asphyxia. Many side products are also formed using this nitrosating agent, thus hampering the recovery of the desired dioximinoketones.

If $\alpha,\alpha'$-dioximinoketones, such as disclosed in the foregoing U.S. patents, could be derived from enamines derived from secondary amines and ketones, particularly cycloaliphatic ketones, and if this conversion could, in addition, be accomplished in nearly quantitative yields, including recycling of the products formed with the desired dioximino ketones to produce additional reactant enamine, a novel, unexpected, inexpensive and practical means would be achieved for preparation of compounds of known and valuable utility that would constitute a significant advance in the state of the art.

SUMMARY OF THE INVENTION

It is, therefore, a general object of the invention to provide a novel, efficacious and inexpensive process for producing dioximinoketones, and specifically, $\alpha\alpha'$-dihydroxyiminocycloalkanones.

It is a further objective of the invention to provide a method for preducing the foregoing dioximino ketones utilizing relatively safe, inexpensive reactants from which the desired dioximino ketones are secured with consistency in optimal yields and wherein the coproducts formed are readily recycled for production of additional end product.

It is consequently an additional object of the invention to avoid the production of unuseable or difficultly separable by-products.

These and other objects and advantages of this invention will become evident from the following description.

Accordingly, it has been discovered that $\alpha\alpha'$-dioximinocycloalkanones containing at least four carbon atoms in the cycloaliphatic ring nucleus can be prepared from an enamine of the corresponding ketone by reaction of the foregoing enamine with nitrosyl chloride in the presence of a small group of empirically selected inert organic solvents.

DESCRIPTION OF THE PREFERRED EMBODIMENTS

The process of this invention comprises therefore reacting an enamine derived from the reaction of a secondary amine and a cycloaliphatic ketone having the general formula:

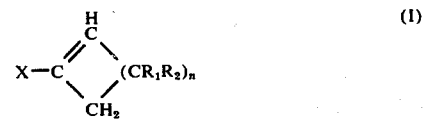

(I)

wherein X is a secondary amino radical, and preferably morpholino; N-alkyl anilino, wherein said alkyl radical contains from 1 to 6 carbon atoms; pyrrolidono; piperidino; and pyrazolino; each of $R_1$ and $R_2$ is hydrogen or a hydrocarbyl radical, and if the latter preferably a lower alkyl moiety of from 1 to 6 carbon atoms; and n is an integer of from 2 to 15 carbon atoms; with nitrosyl chloride in a selected group of empirically derived solvents (defined below), until the corresponding 2,6-dioximinocycloalkylidene-containing quaternary ammonium chloride adduct is formed. At the end of this time the adduct is sequentially hydrolyzed to produce the desired and corresponding 2,6-dioximino-1-cycloalkanone. At least one mole equivalent, and most desirably, slightly in excess thereof, of nitrosyl chloride for each mole of enamine is introduced into the reaction mixture. Normally no more than three mole equivalents of nitrosyl chloride for each mol of enamine is utilized since increased amounts of nitrosyl chloride are not productive of greater yields of the desired product but tend to lead only to undesired side reactions. The product oximinocycloalkanones coming within the practice of the invention are represented by the following general formula:

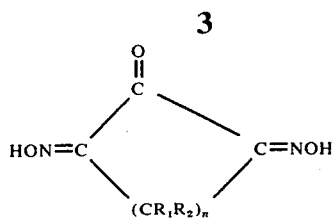

(II)

wherein $R_2$, $R_3$ and n have the values assigned hereinabove with respect to formula I.

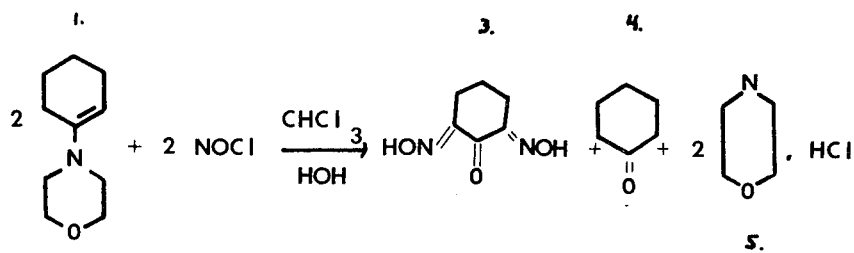

Particularly preferred of the enamines are 1-morpholino-1-cyclohexene, 1-pyrrolidino-1-cyclohexene, 1-pyrrolidino-1-cyclopentene, and 1-pyrrolidino-1-cyclopentene; that is, those enamines coming within formula I wherein each of $R_1$ and $R_2$ is hydrogen; n is either 2 or 3 and X is morpholino or pyrrolidino.

Particularly preferred of the dioximinocycloalkanones prepared according to the practice of the invention are 2,6-dioximino-1-cyclohexanone and 2,5-dioximino-1-cyclopentanone.

Other enamines desirably employed in the practice herein described are 1-piperidino-1-cyclohexene, 1-piperidino-1-cyclopentene, 1-pyrazolino-1-cyclopentene, 1-[N-methylanilino]-1-cyclohexene, 1-[N-ethylanilino]-1-cyclopentene and 1-[N-ethylanilino]-1-cyclohexene; that is, those enamines of formula I wherein each of $R_1$, $R_2$ and n retain the values specified with respect to particularly preferred morpholino and pyrrolidino enamines but X is selected additionally from piperidino; pyrrazolino; and an N-alkyl anilino moiety and in the latter instance, wherein the alkyl radical contains from 1 to 6, and most desirably from 1 to 2 carbon atoms.

The reactant enamines of formula I are well-known and readily available to those skilled in the art conventionally, as suggested hereinabove, by reaction of a ketone with a secondary amine. In addition, the amine reactant must contain minimally at least one aliphatic hydrocarbon constituent and within the scope of this invention is a cycloaliphatic radical.

Illustratively, cyclohexanone may be reacted with morpholine by refluxing these reactants in toluene for a period of about three hours at a temperature of about 110° Centigrade (°C) to yield the preferred enamine reactant, 1-morpholino-1-cyclohexene, in a yield of about 94 percent together with water which is readily removed therefrom.

The reaction provided by the instant invention takes place in the presence of an inert atmosphere, for example, nitrogen, at atmospheric pressure using one mole equivalent of nitrosyl chloride to reactant enamine; and two mole equivalents of each. Most desirably a slight excess of nitrosyl chloride should be employed. The reaction proceeds at a temperature within the range of 0°C to 50°C and preferably at about 0° to 25°C in the presence of a solvent selected from the group consisting of chloroform, and alkanols containing 1 to 4 carbon atoms. Chloroform represents the preferred solvent since it consistently produces good yields of the desired product under mild reaction temperatures.

A base in addition to the reactant enamine, and preferably an amine base such as triethylamine, or morpholine may be included optionally in the reaction mixture.

The sequence involved in securing the products of the invention may be illustrated by the following composite reaction in which 1-morpholino-1-cyclohexene is used, illustratively, as the reactant base.

It will be evident as explained heretofore that any of the other enamines embraced by formula I above may be substituted in the foregoing reaction. The cyclohexanone and morpholine hydrochloride formed are readily separated from the reaction product mixture by standard techniques. The morpholine hydrochloride is neutralized prior to this separation and both of these by-products are recycled for preparation of additional enamine for use in producing the desired cycloalkanones of the invention.

It is preferred to use gaseous nitrosyl chloride in the practice of the invention. The use of various reactants which may effectively form nitrosyl chloride in situ is avoided because of the generally significantly reduced effectiveness of the reaction sequence to secure the desired products in high yields and over a practicable time period and the inherent difficulty and danger in handling certain of these compounds.

The present invention is further illustrated by the following examples:

EXAMPLE I

This example illustrates the preparation of 2,6-dioximino-1-cyclohexanone by the process of the invention.

1-Morpholino-1-cyclohexene (18.4 grams, 0.11 mole) was dissolved in 400 milliliters (ml) of dry chloroform and placed in a 1-liter, 3-neck flask fitted with a mechanical stirrer, gas inlet tube, thermometer and condenser. The flask and contents were cooled to 0° to 5°C. A nitrogen atmosphere was maintained above the solution at all times during the reaction. The gaseous nitrosyl chloride in an amount of 0.11 mole was admitted to the flask through the inlet tube positioned just above the surface of the stirred solution. It was added at a rate of 102 ml per minute (min.) for a period of 24 minutes. The reaction occurred immediately and the solution turned light brown. A yellow precipitate appeared after 13 minutes. Additional yellow precipitate continued to accumulate at the bottom of the reaction vessel during the foregoing period of 24 minutes in which nitrosyl chloride was being introduced into the reactor. The mixture was stirred for 10 minutes and 40 ml of ice water was added rapidly. The precipitate in turn dissolved rapidly and after a period of 1 to 2 minutes, a further yellow precipitate newly appeared in copious amounts. This precipitate, 2',6'-dioximinocyclohexanone, was filtered and recrystallized from a fifty percent by volume solution of aqueous methanol to yield 8.40 grams of a yellow precipitate which was identical to an authentic sample of 2,6-dioximinocyclohexanone, as shown by melting point (m.p.) infrared (I.R.) and nuclear magnetic resonance (N.M.R.) spectral analysis. The yield of 2,6-dioximinocyclohexanone thus secured was 97.5 mole percent based on the nitrosyl chloride charged. Morpholine hydrochloride and cyclohexanone were recovered in yields of 99 mole percent and mole 98 percent from the water and chloroform layers formed in the reaction vessel upon completion of the reaction.

Under comparable reaction conditions, the process above is repeated using methanol, ethanol, n-propanol and n-butanol, in separate runs, instead of chloroform. In all instances, fair to moderate yields of the desired product are obtained.

EXAMPLE II

This example illustrates the preparation of 2,6-dioximino-1-cyclohexanone using an increased amount of nitrosyl chloride.

The procedure of Example I was repeated utilizing 0.26 moles of reactant nitrosyl chloride. There was recovered, after drying, 11.90 grams of 2,6-dioximinocyclohexanone which corresponds to a crude yield of 70 mole percent based on the enamine charged.

It will be evident that the terms and expressions which have been employed are used as terms of description and not of limitation. There is no intention in the use of such terms and expressions of excluding equivalents of the features shown and described or portions thereof and it is recognized that various modifications are possible within the scope of the invention claimed.

What is claimed is:

1. A process of producing a 2,6-dioximino-1-cycloalkanone product by reacting an enamine corresponding to the formula:

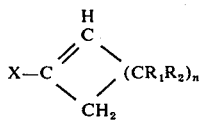

wherein X is a secondary amino radical selected from the group consisting of morpholino, N-alkyl anilino wherein said alkyl radicals contain from 1 to 6 carbon atoms, pyrrolidino; piperidino and pyrazolino; each of $R_1$ and $R_2$ is hydrogen or lower alkyl radical containing from 1 to 6 carbon atoms, and n is an integer of from 2 to 15 carbon atoms; with nitrosyl chloride in an inert organic solvent selected from the group consisting of chloroform and alkanols containing 1 to 4 carbon atoms, until a 2,6-dioximinocycloalkylidene-containing quaternary ammonium adduct of said amine is formed and hydrolyzing said adduct to the desired 2,6-dioximino-1-cycloalkanone.

2. The process as claimed in claim 1 wherein at least one mole equivalent of nitrosyl chloride is reacted with each mole of said enamine.

3. The process as claimed in claim 2 wherein an amount slightly in excess of one mole equivalent of nitrosyl chloride per mole of reactant enamine is introduced into the reaction mixture.

4. A process as claimed in claim 1 wherein said solvent is chloroform.

5. A process as claimed in claim 4 wherein the temperature of the reaction is maintained within a range of 0° to 50°C.

6. A process as claimed in claim 5 wherein each of $R_1$ and $R_2$ is hydrogen or a lower alkyl radical containing from 1 to 6 carbon atoms.

7. A process of producing a 2,6-dioximino-1-cycloalkanone product by reacting an enamine corresponding to the formula:

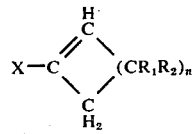

wherein X is a secondary amino radical selected from the group consisting of morpholino; N-alkyl aniline, wherein said alkyl radicals contain from 1 to 6 carbon atoms, pyrrolodino, piperidino, and n is an integer of from 2 to 15 carbon atoms; with at least one mole equivalent of nitrosyl chloride per mole of enamine, at temperatures ranging from 0° to 50°C, in the presence of dry chloroform, until a 2,6-dioximinocycloalkylidene containing quaternary ammonium adduct is formed and hydrolyzing said adduct to the desired 2,6-dioximino-1-cycloalkanone.

8. A process for producing 2,6-dioximino-1-cyclohexanone product by the reaction of 1-morpholino-1-cyclohexene with nitrosyl chloride, by the steps of:
   a. admixing each mole of 1-morpholino-1-cyclohexene with at least a stoichiometric excess of nitrosyl chloride, in dry chloroform, in an inert atmosphere at a temperature ranging from 0° to 25°C until a reaction admixture is formed;
   b. maintaining the temperature of the reaction admixture from 0° to 25°C for a time sufficient to precipitate out a substantial quantity of N-[2',6'-dioximinocyclohexylidene] morpholinium chloride, and
   c. hydrolyzing said N-[2',6'-dioximinocyclohexylidene] morpholinium chloride to the desired 2,6-dioximinocyclohexanone.

9. A process for producing 2,6-dioximino-1-cyclohexanone product by the reaction of 1-morpholino-1-cyclohexene with nitrosyl chloride, by the steps of:
   a. admixing each mole of 1-morpholino-1-cyclohexene with at least a stoichiometric excess of nitrosyl chloride, in dry chloroform, in an inert atmosphere at a temperature ranging from 0° to 25°C until a reaction admixture is formed;
   b. maintaining the temperature of the reaction admixture from 0° to 25°C for a time sufficient to precipitate out a substantial quantity of N-[2',6'-dioximinocyclohexylidine] morpholinium chloride;
   c. hydrolyzing said N-[2',6'-dioximinocyclohexylidine] morpholinium chloride to the desired 2,6-dioximinocyclohexanone;
   d. recrystallizing said 2,6-dioximinocyclohexanone contained therein.

* * * * *